United States Patent
Sullivan

(10) Patent No.: US 6,171,263 B1
(45) Date of Patent: Jan. 9, 2001

(54) FOETAL CIRCULATORY IMPEDANCE MONITOR

(75) Inventor: Colin Edward Sullivan, Birchgrove (AU)

(73) Assignee: The Institute of Respiratory Medicine Limited, New South Wales (AU)

(*) Notice: Under 35 U.S.C. 154(b), the term of this patent shall be extended for 0 days.

(21) Appl. No.: 09/116,574

(22) Filed: Jul. 16, 1998

Related U.S. Application Data

(63) Continuation-in-part of application No. 08/836,923, filed on May 23, 1997, now Pat. No. 5,817,035.

(30) Foreign Application Priority Data

Nov. 24, 1994 (AU) .................................................. PM9640
Nov. 24, 1995 (WO) ................................. PCT/AU95/00789

(51) Int. Cl.[7] ....................................................... A61B 5/02
(52) U.S. Cl. .......................................... 600/588; 600/500
(58) Field of Search ................................... 600/376, 511, 600/561, 588

(56) References Cited

U.S. PATENT DOCUMENTS

| | | | |
|---|---|---|---|
| 3,599,628 | * 8/1971 | Abbenante | 600/588 |
| 3,989,034 | 11/1976 | Hojaiban . | |
| 4,548,204 | * 10/1985 | Groch et al. | 600/588 |
| 4,781,200 | * 11/1988 | Baker | 600/588 |
| 5,140,992 | * 8/1992 | Zuckerwar | 600/588 |
| 5,178,151 | * 1/1993 | Sackner | 600/588 |
| 5,442,940 | * 8/1995 | Secker et al. | 600/589 |
| 5,524,631 | 6/1996 | Zahorian et al. . | |

* cited by examiner

Primary Examiner—Francis J. Jaworski
(74) Attorney, Agent, or Firm—Nixon & Vanderhye

(57) ABSTRACT

A device and method for monitoring a foetus over a period of time. The device includes an electrocardiograph for receiving and processing signals generated by the foetal heart and received from an electrode attached to the abdomen of the mother. The device also includes a second signal receiving and processing means for signals generated by a pressure or acceleration detector that is also attached to the abdomen of the pregnant mammalian animal. The pressure detector produces signals representative of the sounds of foetal heartbeat. The device also includes a comparator means to compare the respective sets of signals, and output means to produce an output indicative of the comparison between the two sets of signals.

32 Claims, 3 Drawing Sheets

FOETAL CIRCULATORY IMPEDANCE MONITOR

This application is a continuation-in-part of application Ser. No. 08/836,923, filed May 23, 1997, now U.S. Pat. No. 5,817,035.

FIELD OF THE INVENTION

The present invention relates to a foetal monitor adapted to provide a measure of foetal circulatory impedance, an index of foetal blood pressure and to a process for measuring such foetal circulatory impedance.

BACKGROUND ART

Foetal development is currently measured in a variety of ways by the midwives and clinicians supervising pregnancy. Current routine measures of foetal development include simple manual methods, such as physical examination by palpation, and auscultation of foetal heart noise; the mother's history, such as date of last menstrual period; the presence or absence of foetal movement ("quickening"); the size of the uterine enlargement; and total maternal weight gain.

These have now been supplemented by advanced technological methods. In particular, diagnostic ultrasound provides a high level of information about the foetus providing a "photographic" like real-time image of the foetus which allows the detection of gross physical abnormality. Diagnostic ultrasound is, however, semi-invasive in that a high frequency soundwave is transmitted into the foetus and the reflected waves are recorded according to how much is absorbed into the foetus or reflected back to the sensor. Although considered safe, there is some uncertainty about potential adverse effects of exposing the foetus to ultrasound over long periods.

Ultrasound use has now been extended to develop a clinical "biophysical profile" in which the heart rate is measured, the presence of foetal breathing movements is sought, and then the presence of spontaneous or evoked (e.g. by manual probing or by externally applied auditory stimuli) foetal body movements. By examining a foetus in this way the attending clinicians are reassured that it is developing normally, or in other cases is identified to be at risk, for example, of placental insufficiency. Although the level of information generated by ultrasound is highly useful and valuable, it provides only a "snapshot" (typically the longest duration being about 20 minutes) of foetus activity in any one day.

While ultrasound can detect abnormalities such as bradycardia and provide a guide to the presence of foetal distress, for example from placental insufficiency, it does not provide a ready means of for quantitatively determining foetal circulatory impedance on a continuous basis or at least over lengthy periods of time (e.g. greater than 20–30 minutes).

Circulation is, of course, a vital function as it constitutes the only means by which cells can receive oxygen and other materials needed for their survival. Similarly, the circulation effects removal of carbon dioxide and other waste products from cells. Blood circulates in the body for the same reason that any fluid flows, i.e. because of pressure gradients that exist in the body. For example, in the heart, blood circulates from the left ventricle to the right atrium of the heart because a blood pressure gradient exists between these two structures. For example, a typical normal blood pressure in the aorta, as the left ventricle contracts pumping blood into it, is 120 mmHg, and as the left ventricle relaxes, it decreases to 80 mmHg with the pressure in the arterial system progressively falling to 0 mmHg by the time blood reaches the venae cavae and right atrium. The progressive fall in pressure as blood passes through the circulatory system is directly related to the resistance offered to the blood flow by the circulatory system. For example, the greatest drop in pressure (about 50 mmHg) occurs across the arterioles because they present the greatest resistance to blood flow.

The primary determinant of arterial blood pressure is the volume of blood in the arteries. Other factors that determine arterial blood pressure include the cardiac output and peripheral resistance of the blood vessels. Cardiac output is determined by both the volume of blood pumped out of the ventricles by each beat (i.e. stroke volume) and by the heart rate. Stroke volume reflects the force or strength of ventricular contraction, i.e. the stronger the contraction, the greater the stroke volume tends to be.

Arterial blood pressure is routinely measured with the aid of a sphygmomanometer which makes it possible to measure the amount of air pressure equal to the blood pressure in an artery. The sphygmomanometer generally consists of a rubber cuff attached by a rubber tube to a compressible bulb and by another tube to a column of mercury that is marked off in millimeters. The cuff is wrapped around the arm over the brachial artery, and air is pumped into the cuff by means of the bulb. In this way, air pressure is exerted against the outside of the artery. Air is added until the air pressure exceeds the blood pressure within the artery and so compresses it. At this time no pulse can be heard through a stethoscope placed over the brachial artery at the bend of the elbow along the inner margin of the biceps muscle. By slowly releasing the air in the cuff the air pressure is decreased until it approximately equals the blood pressure within the artery. At this point the vessel opens slightly and a small spurt of blood comes through producing a first sound. This is followed by increasingly louder sounds that suddenly change. They became more muffled, then disappear altogether. Clinicians listen to these sounds whilst simultaneously reading the column of mercury. The first sound represents the systolic blood pressure. Systolic pressure is the force with which the blood is pushed against the artery walls when the ventricles are contracting. The lowest point at which the sounds can just be heard before they disappear is approximately equal to the diastolic pressure or the force of the blood when the ventricles are relaxed.

Systolic pressure gives valuable information about the force of the left ventricular contraction and diastolic pressure gives valuable information about the resistance of the blood vessels. Clinically, diastolic pressure is considered more important than systolic pressure because it indicates the pressure or strain to which blood vessel walls are constantly subjected. It also reflects the condition of the peripheral vessels since diastolic pressure rises or falls with the peripheral resistance. If for instance arteries are sclerosed, peripheral resistance and diastolic pressure both increase.

While outside the womb, it is readily straightforward to monitor the circulatory system of a human by taking such action as measuring blood pressure and pulse, it is not so straightforward to determine for the foetus in utero. The present invention is directed to one means of monitoring the circulatory condition of a foetus.

DISCLOSURE OF THE PRESENT INVENTION

The present inventor has invented a device and a method whereby a foetus may be monitored in a totally non-invasive manner over a period of time and reported on in a new manner that provides significant additional data to the clinician managing the foetus and its mother. The device and the method will provide the midwife, general practitioner, obstetrician or veterinarian with an objective record of foetal circulatory impedance during pregnancy and so provide another useful method of detecting foetal distress.

The present invention consists in a device for monitoring a foetus including signal processing means having first signal receiving means to receive a first set of electrical signals generated by the foetal heart, and second signal receiving means to receive a second set of electrical signals generated by a pressure or acceleration detector, the detector being capable of generating signals representative of the sounds of foetal heartbeat, comparator means to compare the first set of signals with the second set of signals, and output means to produce an output indicative of the comparison between the two sets of signals.

In another aspect, the invention consists in a method for monitoring a foetus including the steps of detecting a first set of electrical signals generated by the foetal heart, producing from the detector a second set of electrical signals representative of the sounds of the foetal heartbeat, comparing the first set of signals with the second set of signals, and producing an output indicative of the comparison between the two sets of signals during the period of time.

While both the device and method will normally be used with humans, they could be used with equal efficacy to monitor the foetus in other mammalian animals. In horse breeding, for instance, the value of some foals is so high that foetal monitoring is warranted.

Generally, the pressure or acceleration detector is applied to the abdomen of a pregnant mammalian animal.

Similarly, the first set of signals is detected by an electrode applied to the abdomen of the pregnant mammalian animal.

In a preferred embodiment, the first signal receiving means can comprise an electrocardiograph connected to one or more electrodes that are attached to the abdomen of the pregnant mammalian animal. The electrocardiograph electrodes preferably comprise small metal plates that have been moistened with an electroconductive paste and attached to the abdomen.

In a preferred embodiment of the invention, the pressure or acceleration detector can comprise a piezoelectric transducer or an accelerometer comprising an integrated circuit containing a floating piezoelectric transducer. The piezoelectric transducer preferably comprises a synthetic plastics material having piezoelectric properties coated on each face with an electrically conductive layer, such as a metal. The plastics material is preferably polyvinylidene fluoride (hereinafter called PVDF) or an analogue or family derivative thereof. PVDF has a potential frequency response from sub hertz (i.e. less than 1 cycle per second) to terahertz levels. In addition the material is highly sensitive, producing relatively large voltages in response to extremely small movements. It can, for example act as a highly sensitive microphone detecting low levels of sound pressure.

The pressure or acceleration detector configuration may take a number of forms. Direct apposition of the PVDF (e.g. 5–10 cm) against the abdominal surface can be supplemented with an air bubble, or water bubble/bag interface if desired. The latter two formats are available to decrease filtering out of higher frequency components associated with movements of the foetus. Another configuration is the direct apposition of a miniaturised accelerometer version of PVDF in which the PVDF material is "floating" inside an integrated circuit microchip amplifier.

A single PVDF pressure detector held to the abdomen over the foetus by a belt can be utilised, with two wires coming from the PVDF leading to an amplifier and recording system within the second signal receiving means. More complex forms of the invention include more than one PVDF pressure detector, for example on either side, above and below the enlarged abdomen. This advanced form of the invention would utilise differing amplitudes of the same "movement profile signature" and so provide a vector identifying the position or area from which the movement was generated. The wiring for the electrocardiograph electrodes could also be fed through the belt that is wrapped around the abdomen.

The comparator means can preferably compare the time of detection of specific components of the first and second sets of signals and so provide to the output means a measure of the time difference between the time of detection of the specific components of the sets of signals.

The output means can provide a display of the output in a number of forms, including a display on a video monitor or on paper. The output means preferably can also provide a display that allows the clinician to review the history of the output and so determine if there has been change in the time of detection of the specific components of the respective sets of signals over the period of time. The record and display could utilise analog and digital recorders and paper hard copies. A preferred method would record digitally on disc for later replay or in real-time on a computer screen. The invention includes software for the display of long-term information.

In a particularly preferred embodiment, the monitoring means provides an output of the time difference in detection of the occurrence of a point on an electrocardiogram signal produced by the electrocardiograph and the occurrence of a sound component of the cardiac cycle of the foetal heart such as that produced by the contraction of the ventricles and also by vibrations caused by the closing of the atrioventricular or cuspid valves.

By monitoring of the time difference between occurrence of a point on an electrocardiogram signal P and a sound component of the corresponding heartbeat, it is possible to provide a measure of the circulatory impedance and an index of blood pressure of the foetus. For example, when the placental resistance rises due to say placental insufficiency, greater pressure must be developed in the foetal ventricles. This leads to a lengthening of the time interval between, for instance, occurrence of the P wave in the measured electrocardiogram of the foetus (i.e. when the depolarisation current passes through the musculature of the atria from the sinoatrial (SA) node causing this musculature to contract) and the occurrence of the first sound made by the heart in the cardiac cycle. Any increase in the time difference over the period of time can be monitored by the clinician and allow determination that the foetus may be at risk due to placental insufficiency or for some other reason. Any placental insufficiency can result in the foetus not receiving sufficient oxygen or nutrients. This may lead in the latter stages of pregnancy, for instance to a decision to induce the birth or to conduct a caesarean delivery rather than risk harming the foetus by leaving it in utero. The output means could, for example, also include an alarm designed to issue a warning if an increase in time difference was measured that was a greater than a pre-set limit.

The monitoring time may be short, however it is preferably more than one hour, and can extend over a period of time greater than one day or one week.

It is possible for the second signal receiving means to detect maternal uterine contractions. The output from the signals generated by such contractions may also supply clinically useful information on its own or when combined with other information gathered by the device. It is known, for instance, that uterine contractions can exacerbate placental insufficiency. Thus if uterine contractions are followed by an increase in foetal circulatory impedance, it may be possible for the clinician to take action to avoid serious compromise to the foetus.

The pressure or acceleration detector can also detect fine movements generated by foetus including foetal breathing movements or foetal body movements (e.g. movement of the limb, head, or torso) and convert these fine movements into further sets of electrical signals. Unlike ultrasound, the device according to the present invention is passive, responding simply to the activities of the foetus.

The respective further sets of electrical signals generated by the pressure or acceleration detector can be filtered and so allow the sets of signals representative of different types of movement by the foetus to be separated from one another. In the case of the sets of signals representative of different types of movement, because each of these movements share low frequency components (e.g. 0–11 Hertz), in order to separate the electrical signals each movement (heart, breathing, body) can also be characterised by its high frequency components, and this in turn is used to identify which, for example, component of the 0–5 Hertz movement signal is generated, for example, by head movements and which is generated by breathing movements. A process analogous to the human function of the ear is used to identify the signals. The normal human "ear" (and brain) identifies, characterises, and easily separates noises (for example a human voice) from many different voices in a room and other sources despite the fact that these voices contain a large amount of overlapping sound frequencies. The identity of the voice, which contains mostly overlapping fundamental noise pressure waves, is characterised by "finger print" harmonics for that voice.

The movements generated by the foetus similarly have pressure wave harmonics which permit the separation, identification and then quantification of the breathing movement, heart movement and limb/torso movements. In this regard, the device uses the microphone property of PVDF to essentially "listen" to the foetus and to characterise the "sounds" (mostly inaudible to the human ear) which are generated by the heart but also due to other actions such as breathing and total body or partial body movement. The invention take advantage of the physical properties of the PVDF, which is robust, to characterise the minuscule movements generated by the foetal heart and, if desired, foetal breathing, and the somewhat larger signals generated by foetal body movement, to identify the dominant frequency components of that movement and, by comparison with each movement's time-linked pressure frequency harmonic profile, to positively separate each from the others thus allowing the generation of an electrical signal which can then be recorded and be identified as that of heart, breathing and body movements.

The sets of electrical signals generated by the foetal physiological movements can be processed by digital methods (digital signal processors and computers) in real time. Each characteristic movement pressure profile for heart movement, breathing movement, and body movements can be identified and then used for continuous monitoring of the foetus.

If monitoring the movements of the foetus, including its heartbeat, it may be necessary to firstly verify the detected signals and adjust the initial settings of the digital filtering needed to separate the movement categories by also monitoring the foetus simultaneously with ultrasound. However, when the range of such profiles is established, the settings of the digital signal filters and the sufficient combination of frequencies and amplitudes which characterise each foetal movement profile will be set permanently in the comparator system, or such defined settings will be used in default mode. With the use of digital recording and large computer memory, the option of recording broad band signals is also available, so that off-line re-analysis of the movement profiles can be undertaken. By using multiple pressure detectors and with suitable digital signal processing and computer graphic visual displays, a movement profile map of the foetus can also be generated. This advanced application of the invention will provide additional information about the foetal position and about multiple foetuses.

A further refinement of the invention includes the addition of one or more pressure detectors which are placed away from the foetus on the mother's body. This could include lower side of the thorax, the side of the abdomen, or the back and the upper thigh. Movement signals from these sensors are processed and used by the computer recording system to separate the mother's own breathing, heart and body movements from those generated by the foetus.

The nature of the harness for the detectors is of importance. A combination of belts is one option. Another option is the use of a close fitting undergarment such as pantyhose or "lycra" tights which comfortably and closely fit over the upper legs, pelvic area and abdomen. Where more than detector was utilised, detectors could be sewn, plastic welded, or inserted into tightly fitting pockets at the desired location. Where maternal breathing and heart movements are to be monitored a body suit version could be used, so that detectors are placed at the rib cage and over the heart.

The second signal processing means could be located in a stand-alone portable box into which is plugged an electrical lead from the detector. A miniaturised box worn on a belt, analogous to a "Walkman" (Registered Trade Mark) radio is another form. A miniaturised radio transmitter could also be held within a pocket in the belt, harness, or body suit, and transmit (telemeter) the signal to a local receiver.

BRIEF DESCRIPTION OF THE DRAWINGS

By way of example only, a preferred embodiment of the present invention is described with reference to the accompanying drawings, in which.

BEST MODE OF CARRYING OUT THE INVENTION

Figure 1:
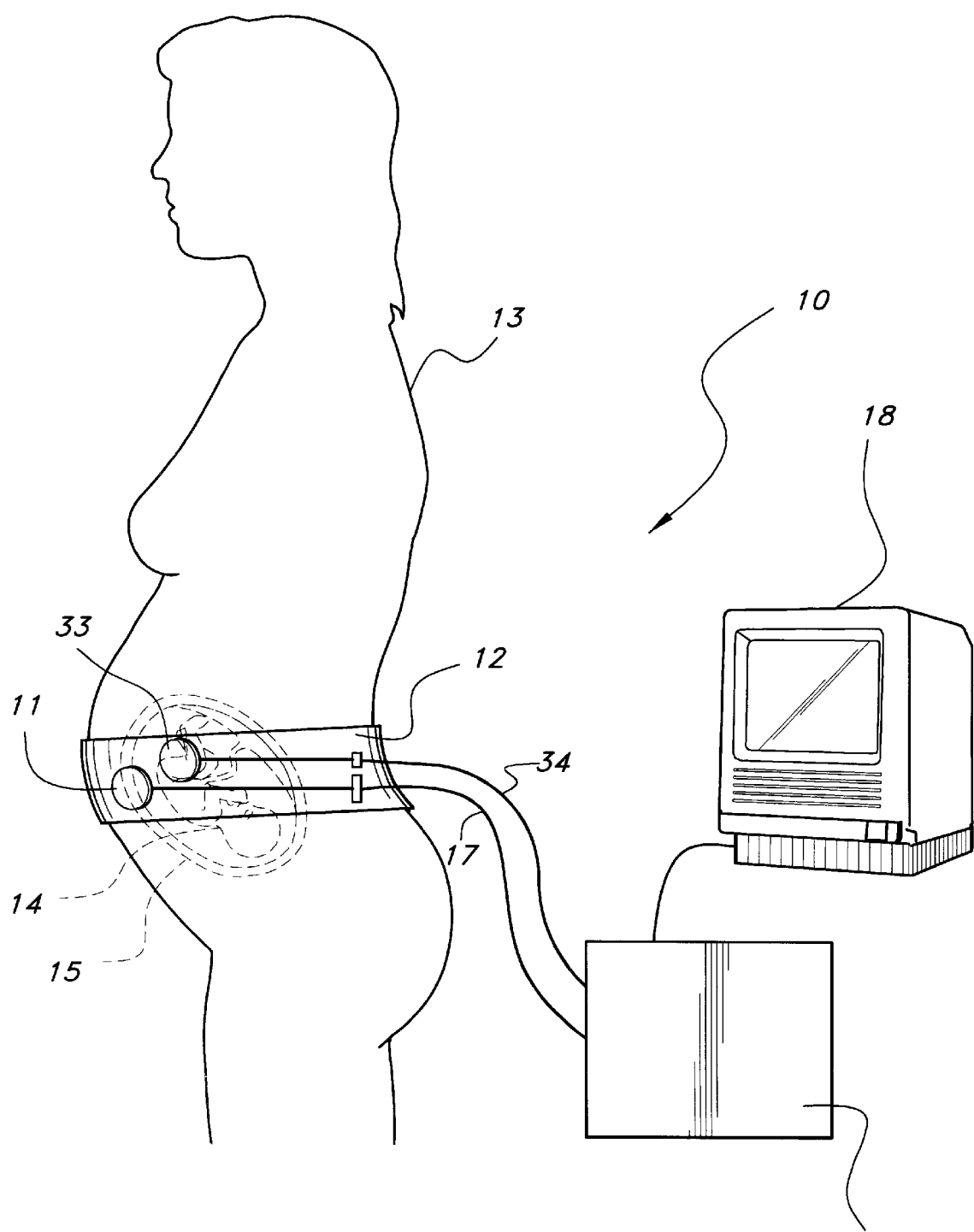
FIG. 1 is a diagrammatic side elevational view of a foetal monitor according to the first embodiment of the present invention.

A device for monitoring a human foetus is generally depicted as 10 in FIG. 1. While adapted to monitor a human foetus, the device 10 could undergo relatively minor modification and be used for the monitoring of the foetus of another mammalian animal, such as a horse.

The device 10 includes a PVDF piezoelectric sensor 11 and electrocardiograph electrode 33 mounted in a belt 12 wrapped around the waist of the mother 13. In use, the belt 12 is adjusted and tightened so as to position the sensor 11 and electrode 33 proximate the position of the foetus 14 in the uterus 15.

The sensor 11 is connected to a processing system 16 by two electrical leads 17 attached between electrodes on the sensor 11 and electrical inputs of the processing system 16. The voltage signals produced by the sensor 11 on the detection of movement by the foetus 14 travel along the leads 17 and are detected by the processing system 16.

The electrode 33 is connected by lead 34 to an electrocardiograph that comprises a component of the processing system 16. The electrocardiograph includes an amplifier that amplifies the electrical signals detected by the electrode 33.

The processing system 16 also includes an amplifier for the signal produced by the sensor 11. The processing system 16 can include a first comparator that compares the amplified voltage signals produced by sensor 11 with an array of previously determined signals characteristic of foetal heartbeat. The processing system also includes a second comparator means that compares the time of detection of signals by the electrode 33 with the time of detection of signals by the sensor 11. In particular, the processing system can determine the time difference between the time of detection of a point on the electrocardiogram signal of the foetal cardiac cycle and a sound component of the corresponding heartbeat.

If necessary, the signal processing system 16 can include a discriminator that can determine signals representative of the cardiac cycle of the foetus from other signals detected by the sensor 11 and electrode 33 including other movements made by the foetus, movements of the mother, maternal contractions, and maternal heartbeat.

While the processing system 16 can discriminate the signals representative of foetal heartbeat from both sensor 11 and electrode 33 from other signals, the processing system 16 can also compare the voltage signals from sensor 11 with an array of previously determined signals characteristic of other potential foetal activities including foetal breathing and foetal body movement to determine if such activities are being made by the foetus during the time of monitoring the foetus.

The processing system can also include a digital recording system and computer memory which allow the signals being detected by the sensor 11 and electrode 33 to be stored for later play back and analysis by a supervising clinician.

The device 10 in FIG. 1 also has a display means 18 comprising a video display unit into which appropriate signals are supplied by the processing system 16. The display means 18 allows real-time display of the signals being captured by the processing system 16 and so provide for immediate analysis of the time difference between detection of the respective signals by the respective sensors 11,33. This analysis then allows a clinician to monitor the circulatory impedance and, if desired, other activities of the foetus 14.

Figure 2:
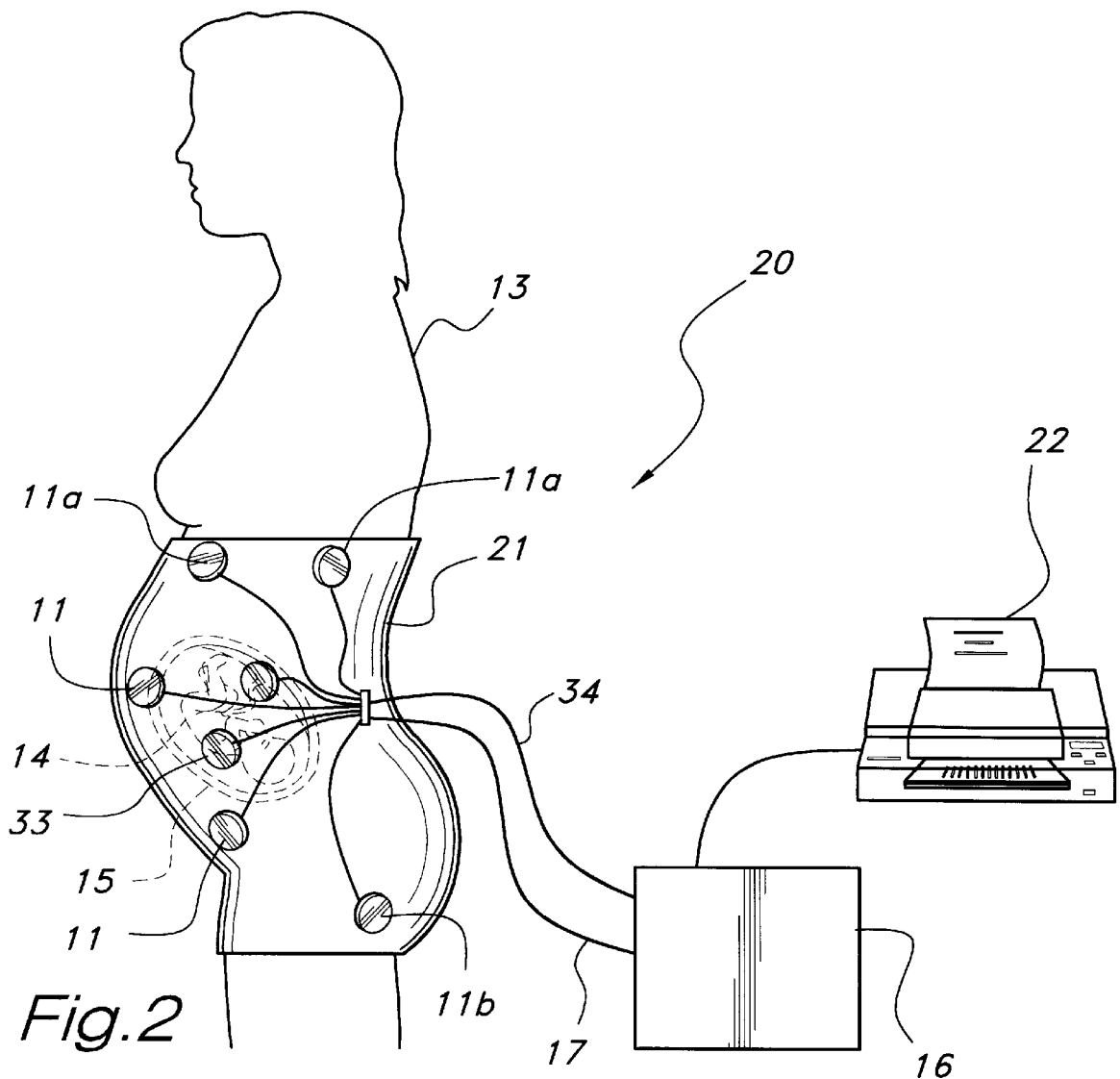
FIG. 2 is a diagrammatic side elevational view of a foetal monitor according to a second embodiment of the present invention.

An alternative device for monitoring a human foetus 14 is generally depicted as 20 in FIG. 2. In this embodiment of the invention, where like features have the same identifying numbers as those given above, the device 20 is adapted to monitor signals from a number of pressure sensors 11 and a electrocardiograph electrode 33.

The device 20 includes a close-fitting undergarment 21 which comfortably and closely fits over the upper legs, pelvic area, abdomen and rib cage of the mother 13. A number of sensors 11 and the electrode 33 are sewn into the undergarment 21 such that when the undergarment 21 is fitted to the mother 13 the sensors 11 and electrode 33 are appropriately placed on the mother 13. Four sensors 11 are positioned for monitoring the foetus 14 (one on each side, one above and one below the uterus 15) so as to provide a vector identifying the position or area from which a movement has originated. Certain sensors are also positioned so as to detect maternal heartbeat and breathing (sensors 11a) and maternal uterine contractions (sensor 11b).

Electrical leads 17 extend between each of the sensors 11, 11a and 11b and a processing system 16. An electrical lead 34 again extends between electrode 33 and processing system 16. The processing system 16 is identical to that described above except that it is adapted to utilise the signals detected by sensors 11a and 11b by subtracting corresponding signals produced by the maternal heartbeat or breathing or uterine contractions from the signals produced by the sensors 11 monitoring the foetus 14.

The processed signal can then be compared by a comparator means with an array of previously determined signals characteristic of potential foetal activity as previously discussed. The differing amplitudes of the signals generated by the sensors 11 monitoring the foetus 14 would be utilised by the processing system 16 to determine the area or position of the movement being detected.

The device 20 also includes a digital recording system and computer memory which allows the signals being detected by the sensors 11, 11a and 11b to be stored for later playback and analysis. The device 20 also has the display means 22 comprising a printer which records the signals detected by the sensors 11, 11a and 11b for immediate analysis.

Figure 3:
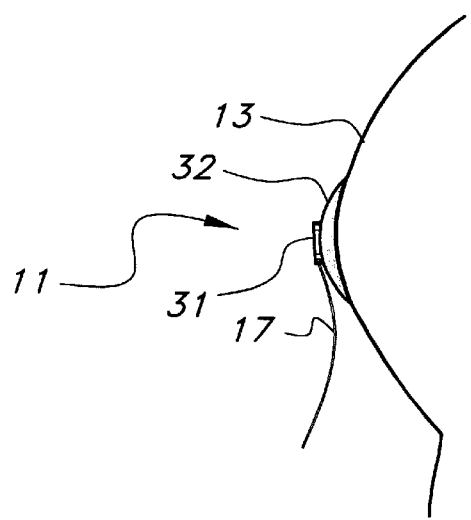
FIG. 3 is a detailed diagrammatic vertical sectional view through a pressure detector for use in the present invention.

As is more clearly depicted in FIG. 3, each sensor 11, 11a or 11b can comprise a PVDF strip 31 attached to a fluid-filled bag 32 which is pressed onto the skin of the mother 13. The fluid-filled bag 32 is used to decrease filtering out of higher frequency components associated with the detected movement.

Both the devices 10 and 20 provide a means of monitoring a foetus 14 over long periods (e.g. greater than 1 day) and so provide a means of determining and monitoring the foetus 14.

Details of experiments undertaken by the inventor using the invention described herein are provided below.

The aim of a first experiment was to determine if it was possible to determine placental insufficiency by determining the circulatory impedance of a foetus with a non-invasive method using a piezoelectric sensor and an electrocardiograph.

A standard amplifier was used to amplify the signal generated by the piezoelectric sensor.

The unfiltered amplified signal was then passed to a digital recording system having a software selectable processing capability, namely the Amlab System produced by Associative Measurement, North Ryde, New South Wales, Australia.

In order to record a large number of physiological variables simultaneously with the abdominal foetal sensor over a long time interval and then to replay this information for analysis, a multi-channel digital polygraphical recording system was used in the experiments. This system which was supplied by Compumedics Pty Limited, Windsor, Victoria, Australia, provided a platform on which to record all the signals and to permit rapid identification of events for easy replay and analysis.

Electrical signals of the foetal heart were measured using a standard electrocardiograph (ECG) machine.

In the first experiment fourteen pregnant sheep were studied. In each case, the pregnant sheep was given an injection of anaesthetic and the level of anaesthetic was assessed throughout the experiment by testing the muscle reflexes of the animal. An intravenous drip of glucose was attached to the anaesthetised sheep. Respiratory conditions and blood pressure were monitored throughout the experiment.

Entrance was gained into the peritoneal cavity through the intra-abdominal skin and muscle. The foetus was then removed from the sheep's abdomen and the umbilical cord carefully exposed. Recording electrodes connected to the ECG were inserted into the foetal back and PVDF sensors were placed on the foetal chest for detecting the sound of the foetal heartbeat.

Once the sensors were attached, the electrical impulses generated by the foetal heart were monitored using the visual display of the electrocardiograph and the sound of the foetal heartbeat was also amplified and monitored using a visual display. The respective signals were monitored so as to allow determination of the time difference between the P wave in the cardiac cycle of the foetal heartbeat and the first heart sound in the cardiac cycle following occurrence of the P wave.

Once the sensors and electrodes were in place, the umbilical cord was repeatedly occluded and then released at measured intervals over a period of time of approximately 1.5–2 hours. Occlusion of the umbilical cord in this manner was designed to replicate an occurrence of placental insufficiency.

As a result of this experiment, it was noted that the interval of time between the P wave of the ECG signal and the first heart sound was influenced by the length of time that the umbilical cord was occluded and the frequency of the occlusions in any one experiment, with the length of time increasing with an increase in the length of time of occlusion.

While monitoring the ECG and heart sounds, experiments were performed that confirmed that after occluding of the umbilical cord hypoxaemia would develop which would gradually develop into acidaemia.

The experiment conducted on the sheep confirmed that placental insufficiency leading to circulatory impedance could be measured using the device as defined herein.

In a second set of experiments foetal human heart movement was recorded using the piezoelectric sensor. Two human subjects were studied, firstly in a series of afternoon studies, and then in all night sleep study. Both foetal movement sensors and heart movement sensors were tested. In a number of experiments electrodes were also placed on the maternal abdomen to record foetal electrocardiogram.

Figure 4:
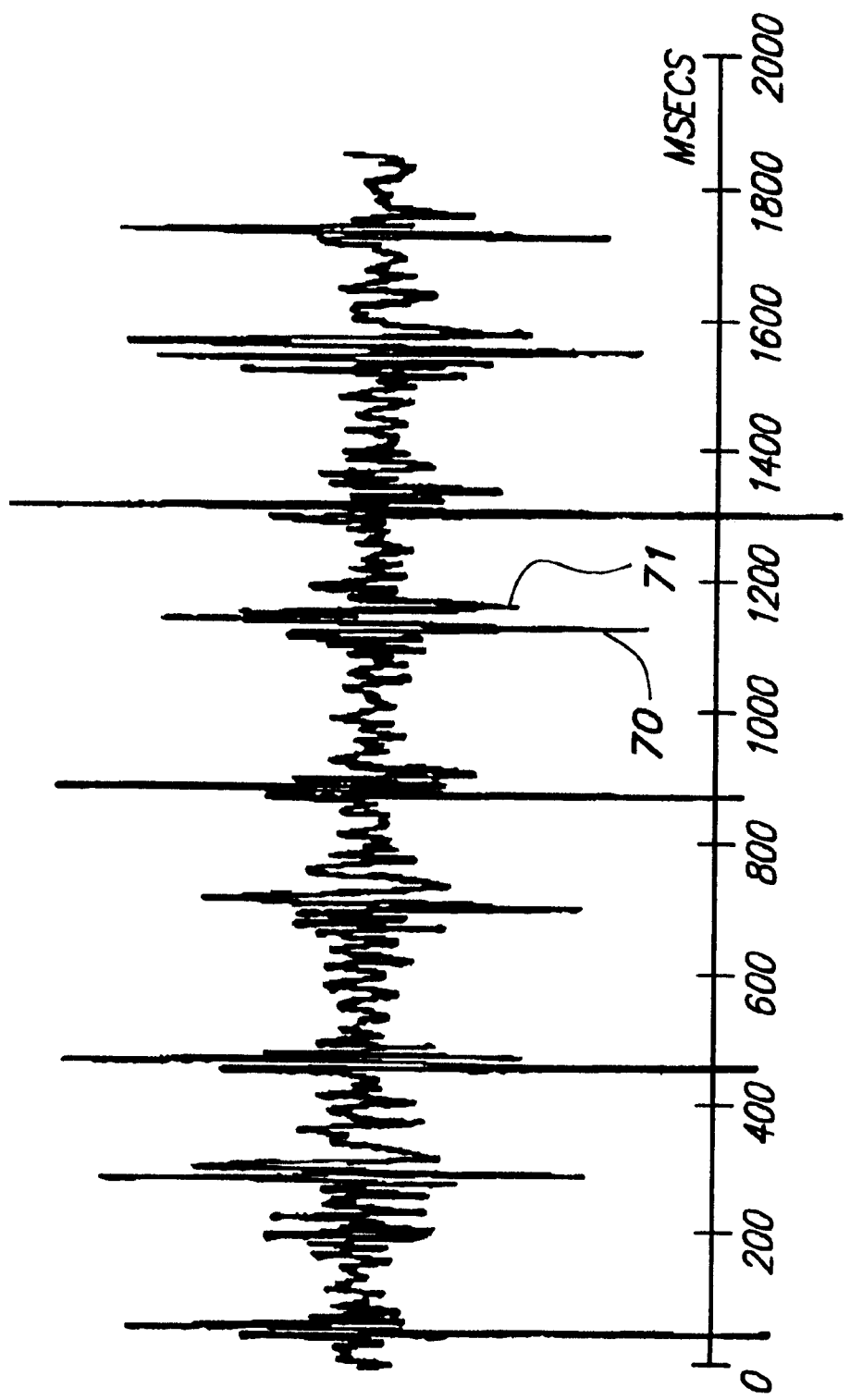
FIG. 4 is an amplitude versus time print-out from a device according to the present invention depicting foetal heartbeat as detected by a piezoelectric pressure detector.

In the second set of experiments, the foetal heart was readily detected. A double movement was found which likely corresponds to heart valve opening and closure (see peaks 70 and 71, respectively in FIG. 4). The amplitude of the signal was variable being sensitive to the site of electrode placement. When the foetus moved position, the amplitude changed.

Heart rate accelerations were clearly recognisable in response to foetal movement.

During all night sleep studies, the heart beat was recorded throughout the night. When large foetal movement occurred, there was clear acceleration of the heart rate.

Notably, there were long periods where the heart beat signal amplitude remained constant, and then following a large movement, the amplitude lessened, and then remained at a new steady level over long periods. The foetal electrocardiogram could be identified, but in general it was of only a small fraction of the amplitude of the maternal ECG. However, when it was visible, it correlated clearly with the heart movement signal.

The results of the second experiment demonstrated that it is possible to record heart impulses continuously with a surface movement sensor. In particular, it was possible to demonstrate the normal heart rate accelerations which occur during foetal movement.

An additional novel finding was that there was a clear change in the amplitude of the signal after some gross foetal movements. This was almost certainly the result of the foetus turning from one side to the other. Because the signal which is produced in the sensor in response to the foetal heart movement is so stable, the amplitude produced by the heart movement sensor offers important information. Thus by identifying a change in the signal amplitude, it is possible to provide an indication that the foetus has changed positions.

Further, because the sensor signal is detecting movements generated by the mechanical action of the foetal heart, it will also detect changes in the foetal heart function; for example, alterations in foetal heart contractility are identifiable, making this an important diagnostic indicator.

Finally, by measuring the time interval between the P wave of the foetal electrocardiogram and the first heart movement signal, it is possible to provide a quantitative index of the circulatory impedance. For example when the placental resistance rises (in placental insufficiency), greater pressure must be developed in the foetal ventricles; this leads to a lengthening of the time interval between the electrical signal (the ECG P wave), and the first heart sound.

It can be seen that this new method of monitoring foetal physiological function can also be used to determine how uterine contraction might compromise the foetus. It is known that uterine contraction can compress the placenta and reduce foetal blood flow, particularly where there is placental insufficiency. This becomes particularly important in the last weeks of pregnancy. The ability to detect foetal bradycardia in response to uterine contraction would provide a useful method of detecting placental insufficiency. A combination of sensors designed to detect foetal movements, heart rate etc, and to simultaneously identify placental contraction will be possible using these new sensor methods.

When appropriately tuned to record fine movement, a variation of the new movement sensors will detect signals generated by maternal placental artery blood flow, and placental blood flow itself. When there is partial obstruction of blood flow through any vessel, turbulence occurs; turbulence then produces a considerable amount of pressure energy which is dissipated as vibration of the vessel wall. This vessel wall vibration, in turn dissipates into the surrounding tissues, sending out pressure waves. When appropriately amplified and tuned, abnormal placental blood flow is recordable on the maternal abdominal wall. When these measures are combined with the other signals of foetal function a comprehensive monitoring device for tracking the well-being of both the mother and foetus will be possible.

By the early identification of placental insufficiency, and in turn the early signs of foetal distress, appropriate intervention can be undertaken, for example early delivery, or, in some cases suppression of uterine contraction and delaying of labour.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A device for monitoring the circulatory impedance of a foetus, the device comprising:
    signal processing means having first signal receiving means to receive a first set of electrical signals generated by the foetal heart;
    second signal receiving means to receive a second set of electrical signals generated by a pressure or acceleration transducer means, the transducer means being capable of generating signals representative of the sounds of the foetal heart;
    comparator means that compares the time of detection of detection of specific components of the first and second sets of signals, and provides a measure of the time difference between the times of detection of said specific components of the sets of signals; and
    output means that receives said measure from the comparator means and displays an output in a form that allows monitoring of the circulatory impedance of the foetus.

2. The device as claimed in claim 1 in which the second signal receiving means is connected directly to the pressure or acceleration transducer means.

3. The device as claimed in claim 2 in which the pressure or acceleration transducer means is selected from the group consisting of a pressure detector comprising a piezoelectric transducer and an accelerometer comprising an integrated circuit containing a floating piezoelectric transducer.

4. The device as claimed in claim 3 in which the pressure or acceleration transducer means is adapted to be applied to the abdomen of a pregnant mammalian animal.

5. The device as claimed in claim 3 in which the piezoelectric transducer is a piezoelectric synthetic plastics material.

6. The device as claimed in claim 5 which the piezoelectric synthetic plastics material is polyvinylidene fluoride (PVDF).

7. The device as claimed in claim 5 which the piezoelectric transducer is mounted on one side of a fluid filled container which is adapted to be applied on its other side to the abdomen of a pregnant mammalian animal.

8. The device as claimed in claim 1 in which the second signal receiving means is connected directly to relay means for replaying a broad band signal derived from the pressure or acceleration transducer means.

9. The device as claimed in claim 1 in which the second signal receiving means includes an amplifier.

10. The device as claimed in claim 1 in which the signal receiving means includes means to remove unwanted signals.

11. The device as claimed in claim 1 in which the comparator means contains previously determined signals characteristic of activities selected from the group comprising foetal breathing, foetal body movement, foetal heartbeat and maternal uterine contractions.

12. The device as claimed in claim 1 in which the second signal receiving means is adapted to receive signals from a plurality of detectors.

13. The device as claimed in claim 12 in which the second signal receiving means is adapted to receive signals from additional detectors placed on the body of the pregnant animal other than on the abdomen.

14. The device as claimed in claim 13 in which the second signal processing means includes means to utilise the signals received from the additional detectors to remove unwanted signals produced by the detectors on the animal's abdomen.

15. The device as claimed in claim 1 in which the first signal receiving means is an electrocardiograph.

16. The device as claimed in claims 15 wherein said measure of the time difference provided by the comparator means is a measure of the time difference in detection of the occurrence of a point on an electrocardiogram signal produced by the electrocardiograph and the occurrence of a sound component of the cardiac cycle of the foetal heart produced by the contraction of the ventricles and also by vibrations caused by the closing of the atrioventricular or cuspid valves.

17. The device as claimed in claim 16 wherein an increase in said time difference is indicative of an increase in foetal circulatory impedance.

18. The device as claimed in claim 17 in which the output means initiates an alarm if the increase in time difference is greater than a pre-set limit.

19. The device as claimed in claim 1 in which the first set of signals is detected by an electrode applied to the abdomen of a pregnant mammalian animal.

20. The device as claimed in claim 19 wherein the electrode comprises a small metal plate that has been moistened with an electroconductive paste and attached to the abdomen.

21. The device as claimed in claim 1 wherein the detectors and electrodes are attached to a belt or harness wrapped around the pregnant mammalian animal.

22. The device as claimed in claim 1 in which the comparator means compares the time of detection of specific components of the first and second sets of signals and so provides to the output means a measure of the time difference between the time of detection of the specific components of the sets of signals.

23. The device as claimed in claim 1 wherein the output means provides a display of the output on a video monitor and/or on paper.

24. The device as claimed in claim 23 wherein the output means records its output digitally on disc for later replay.

25. The device as claimed in claim 1 in which the device monitors a foetus over an extended period of time.

26. A device for monitoring the circulatory impedance of a foetus, the device comprising:
    signal processing device having a first signal receiver for receiving a first set of electrical signals generated by the foetal heart;
    second signal receiver for receiving a second set of electrical signals generated by a pressure or acceleration transducer capable of generating signals representative of the sounds of the foetal heart;
    a comparator that compares the time of detection of detection of specific components of the first and second sets of signals, and provides a measure of the time difference between the times of detection of said specific components of the sets of signals; and
    an output device that receives said measure from the comparator and displays an output in a form that allows monitoring of the circulatory impedance of the foetus.

27. A method for monitoring a foetus comprising the steps of:
- detecting with a detector a first set of electrical signals generated by the foetal heart;
- producing from the detector a second set of electrical signals representative of the sounds of the foetal heartbeat;
- comparing the first set of signals with the second set of signals; and
- producing an output indicative of the comparison between the two sets of signals during the period of time.

28. The method as claimed in claim 27 in which the first set of electrical signals are detected by an electrode applied for a period of time to the abdomen of a pregnant mammalian animal.

29. The method as claimed in claim 27 in which the second set of electrical signals are produced by a pressure or acceleration detector applied for a period of time to the abdomen of a pregnant mammalian animal.

30. The method as claimed in claim 27 in which the foetus is monitored for a period of time of at least one hour continuously.

31. The method as claimed in claim 30 in which the foetus is monitored for a period of time of at least one day substantially continuously.

32. The method as claimed in claim 31 in which the foetus is monitored for a period of time of at least one week substantially continuously.

* * * * *